US009717250B2

(12) United States Patent
Thompson et al.

(10) Patent No.: US 9,717,250 B2
(45) Date of Patent: Aug. 1, 2017

(54) ISOTHIAZOLINONE BIOCIDES ENHANCED BY ZINC IONS

(71) Applicant: Arch Chemicals, Inc., Norwalk, CT (US)

(72) Inventors: Nicholas Edward Thompson, Lancashire (GB); Malcolm Greenhalgh, Ripponden (GB); Fitzgerald Clarke, Manchester (GB)

(73) Assignee: ARCH CHEMICALS, INC., Norwalk, CT (US)

( * ) Notice: Subject to any disclaimer, the term of this patent is extended or adjusted under 35 U.S.C. 154(b) by 130 days.

(21) Appl. No.: 13/850,672

(22) Filed: Mar. 26, 2013

(65) Prior Publication Data

US 2013/0287863 A1    Oct. 31, 2013

Related U.S. Application Data

(62) Division of application No. 11/805,779, filed on May 24, 2007.

(60) Provisional application No. 60/808,697, filed on May 26, 2006.

(30) Foreign Application Priority Data

May 26, 2006   (WO) ............... PCT/US2007/012518

(51) Int. Cl.
| *A01N 59/16* | (2006.01) |
| *A01N 43/80* | (2006.01) |
| *A61K 31/425* | (2006.01) |
| *A61K 31/555* | (2006.01) |
| *A61K 33/30* | (2006.01) |

(52) U.S. Cl.
CPC ............ *A01N 59/16* (2013.01); *A01N 43/80* (2013.01); *A61K 31/425* (2013.01); *A61K 31/555* (2013.01); *A61K 33/30* (2013.01)

(58) Field of Classification Search
CPC ...... A01N 59/16; A01N 43/80; A61K 31/425; A61K 31/555; A61K 33/30
See application file for complete search history.

(56) References Cited

U.S. PATENT DOCUMENTS

| 3,403,119 A | 9/1968 | Sullivan et al. |
| 3,976,501 A | 8/1976 | Blue |
| 4,031,055 A | 6/1977 | Dupont et al. |
| 4,150,026 A * | 4/1979 | Miller .................... A01N 43/80 504/152 |
| 4,241,214 A | 12/1980 | Miller et al. |
| 4,299,749 A | 11/1981 | McCarthy et al. |
| 5,059,456 A | 10/1991 | Larson et al. |
| 5,125,967 A | 6/1992 | Morpeth et al. |
| 5,208,272 A | 5/1993 | Lesota |
| 5,221,530 A | 6/1993 | Janchitraponvej et al. |
| 5,227,156 A * | 7/1993 | Wiese ........................... 514/345 |
| 5,290,810 A | 3/1994 | Austin |
| 5,696,083 A | 12/1997 | Nelson, Jr. |
| 5,723,112 A | 3/1998 | Bowser et al. |
| 5,840,790 A | 11/1998 | Ong |
| 5,883,154 A | 3/1999 | Kappock et al. |
| 6,133,300 A | 10/2000 | Smith et al. |
| 6,156,108 A | 12/2000 | Wachowiak, Jr. |
| 6,433,056 B1 * | 8/2002 | Burdick et al. ............... 524/394 |
| 6,455,558 B1 | 9/2002 | Bath et al. |
| 7,025,952 B1 | 4/2006 | Traynor et al. |
| 2004/0014736 A1 | 1/2004 | El A'mma et al. |
| 2004/0014799 A1 | 1/2004 | Antoni-Zimmermann et al. |
| 2004/0198713 A1 | 10/2004 | Heer et al. |
| 2005/0065232 A1 * | 3/2005 | Okimoto et al. ............. 523/122 |
| 2005/0101487 A1 * | 5/2005 | Beilfuss ................. A01N 43/70 504/134 |
| 2005/0197366 A1 | 9/2005 | Chia et al. |
| 2006/0009553 A1 | 1/2006 | Sin |
| 2006/0111410 A1 | 5/2006 | Wachtler et al. |
| 2007/0275945 A1 | 11/2007 | Lindner |

FOREIGN PATENT DOCUMENTS

| EP | 0249328 | 12/1987 |
| EP | 0425143 | 5/1991 |
| EP | 0455379 | 11/1991 |
| EP | 0492811 | 7/1992 |
| EP | 1527685 | 5/2005 |

(Continued)

OTHER PUBLICATIONS

Bulmer et al., Te antifungal action of dandruff shampoos, Mycopathologia 147: 63-65, 1999.
Simpson et al, Long term protection with fungicide and algaecide development, Additives for Waterborne Coatings, PPCJ, 1996.
Mattei et al., Formulating Stable Latex Paints With Zinc Oxide, Presented at the 68th Annual meeting of the Federation of Societies for Coatings Technology in Washington D.C., 1991.
Examination Report of EP07809194.9, Dated Jan. 29, 2015.
Third Party Observations in EP07809194.9, Dated Dec. 3, 2014.
Third Party Observations for EP 07809194.9, Dated Feb. 27, 2015.

(Continued)

*Primary Examiner* — Ali Soroush
(74) *Attorney, Agent, or Firm* — Dority & Manning, PA (57) ABSTRACT

The present invention relates to an antimicrobial composition comprising an isothiazolinone, such as 1,2-benzisothiazolin-3-one, and a zinc compound selected from zinc salts, zinc oxides, zinc hydroxides or combinations thereof. Useful zinc salts include for example, oxides, sulfates, chlorides, and combinations thereof. In use, the zinc from the zinc compound enhances the antimicrobial activity to the isothiazolin-containing composition. This enhancement permits achieving the desired antimicrobial activity at a lower usage rate than is achieved using the isothiazolinone in the absence of the zinc compound. The antimicrobial composition can also contain co-biocides, such as pyrithiones, including zinc pyrithione or copper pyrithione.

10 Claims, 5 Drawing Sheets

(56) References Cited

FOREIGN PATENT DOCUMENTS

| | | |
|---|---|---|
| GB | 2200846 | 8/1988 |
| GB | 2230190 | 10/1990 |
| JP | 57156405 | 9/1982 |
| JP | S62-070301 | 3/1987 |
| JP | H04-273852 | 9/1992 |
| JP | H08-231317 | 9/1996 |
| JP | H09-301805 | 11/1997 |
| JP | 2003-055116 | 2/2003 |
| JP | 2004-051635 | 2/2004 |
| JP | 2005-281305 | 10/2005 |
| WO | WO 92/01380 | 2/1992 |
| WO | WO 94/03146 | 2/1994 |
| WO | WO 95/00019 | 5/1995 |
| WO | WO 96/22023 | 7/1996 |
| WO | WO 99/65315 | 12/1999 |
| WO | WO 00/38520 | 7/2000 |
| WO | WO 2004014416 | 2/2004 |
| WO | WO 2004/099308 | 11/2004 |
| WO | WO 2007/139645 | 12/2007 |

OTHER PUBLICATIONS

Proxel® BZ Preservative Technical Sheet, EPA Accepted Date of Apr. 22, 1999.
Proxel® BZ Preservative Technical Sheet, EPA Accepted Date of Feb. 27, 2002.
Third Party Observations for EP 07809194.9, Dated Jun. 8, 2016.
Third Party Observations for EP 07809194.9, Dated Jun. 23, 2016.

* cited by examiner

ISOTHIAZOLINONE BIOCIDES ENHANCED BY ZINC IONS

CROSS REFERENCE TO RELATED APPLICATIONS

This application is a division of U.S. application Ser. No. 11/805,779, filed on May 24, 2007; PCT application PCT/US07/12518 filed on May 25, 2007; and provisional application 60/808,697 filed on May 26, 2006 the entire contents of each of which are hereby incorporated in total by reference.

BACKGROUND OF THE INVENTION

Isothiazolinones, such as 1,2-benzisothiazolin-3-one (also referred to as "BIT"), are know to be effective antimicrobials. BIT, as disclosed for example in formulations described in European patent EP 0 703 726, is widely used as a bactericide in a variety of applications. Illustratively, British patent publication GB2,230,190A discloses a preservative composition containing BIT and an adduct of zinc chloride ("ZC"), together with 2,2'-dithiopyridine-1,1'-dioxide ("DTP"). Example 3 of '190A publication compares compositions containing BIT plus ZC plus DTP against a control example containing only BIT plus ZC. The results given in Example 3 and Table 3 of the publication indicate that inclusion of DTP allows decreased usage of BIT in the composition. Nonetheless, the amount of BIT (2.5 ppm) employed in the control example has been found by the present inventors to be insufficient for antimicrobial efficacy in real-world applications.

While BIT has proven useful in a wide range of applications, the useful amount of BIT that can be added to a commercial product is limited by efficacy and economic considerations and to a lesser extent by environmental and toxicological concerns. Accordingly, alternative antimicrobial compositions are needed for wet state applications that are cost-effective and minimize the likelihood of adverse environmental and toxicological effects. The present invention provides one such alternative.

SUMMARY OF THE INVENTION

In one aspect, the present invention relates to an antimicrobial composition comprising (a) at least one isothiazolin-3-one and (b) at least one zinc compound selected from the group consisting of zinc salts, zinc oxides, zinc hydroxides, and combinations thereof. Illustrative zinc salts are zinc chloride, zinc sulfide, zinc carbonate, basic zinc carbonate, and combinations thereof. The zinc compound provides a source of metal ion in the antimicrobial composition. In the composition, the isothiazolin-3-one is present in an amount of from 1 to 500 ppm (preferably from 5 to 500 ppm), the zinc compound is present in an amount from 5 to 200,000 ppm (preferably from 5 to 500 ppm), and the weight ratio of the isothiazolin-3-one to the zinc compound is from 1:2000 to 100:1 (preferably from 1:100 to 100:1). Optionally, the antimicrobial composition additionally comprises a pyrithione salt or pyrithione acid. Useful pyrithione salts include copper pyrithione, zinc pyrithione, sodium pyrithione, pyrithione disulfide, and combinations thereof.

In another aspect, the present invention relates to an antimicrobial composition concentrate that, upon dilution with water, provides antimicrobial efficacy in a functional fluid. The concentrate comprises (a) at least one isothiazolin-3-one and (b) at least one zinc compound selected from the group consisting of zinc salts, zinc oxides, zinc hydroxides, and combinations thereof. In the concentrate, component (a) is present in an amount of from 1 to 95% w/w, and component (b) is present in an amount of from 1 to 50% w/w based on the total weight of the concentrate, with the proviso that the weight percent of (a) plus (b) does not exceed 100% by weight.

In yet another aspect, the present invention relates to functional fluid that comprises a base medium plus (a) at least one isothiazolin-3-one and (b) at least one zinc compound selected from the group consisting of zinc salts, zinc oxides, zinc hydroxides, and combinations thereof. Illustrative zinc salts are zinc chloride, zinc sulfide, zinc carbonate, basic zinc carbonate, and combinations thereof. In the composition, the isothiazolin-3-one is present in an amount of from 1 to 500 ppm (preferably from 5 to 500 ppm), the metal compound is present in an amount of from 5 to 20,000 ppm (preferably from 5 to 500 ppm), and the weight ratio of the isothiazolin-3-one to zinc ion is from 1:2000 to 100:1 (preferably from 100:1 to 1:100). Optionally, the antimicrobial composition additionally comprises a pyrithione salt or pyrithione acid. Useful pyrithione salts include copper pyrithione, zinc pyrithione, sodium pyrithione, and pyrithione disulfide. The base medium for the functional fluid can be, for example, a polymer useful in polymer emulsions. Examples of polymer systems are lattices, such as acrylic and substituted (meth)acrylates, styrene/butadiene, ethylene vinyl acetate, polyvinyl acetate, styrene/butadiene/N-methylol acrylamide, nitrile and copolymers of the aforementioned. Typical functional fluids include coating compositions, such as paints, adhesives, sealants, caulks, mineral and pigment slurries, printing inks, agricultural pesticide formulations, household products, personal care, metal working fluids and other aqueous based systems.

These and other aspects will become apparent upon reading the following detailed description of the invention.

DETAILED DESCRIPTION OF THE INVENTION

It has now been surprisingly found in accordance with the present invention that an antimicrobial composition containing an isothiazolin-3-one, plus a zinc compound selected from the group consisting of zinc salts, zinc oxides, zinc hydroxides, and combinations thereof, exhibits enhanced antimicrobial efficacy, as compared to isothiazolin-containing compositions that do not contain the metal compound. Enhanced efficacy are suitably provided in antimicrobial compositions over a wide range of pHs of from 3 to 12.

The antimicrobial composition of the present invention is suitably incorporated into a functional fluid. The functional fluid suitably comprises a base medium plus (a) at least one isothiazolin-3-one and (b) at least one zinc compound selected from the group consisting of zinc salts of organic acids, zinc salts of inorganic acids, zinc oxides, zinc hydroxides, and combinations thereof. Illustrative zinc salts include zinc chloride, zinc sulfide, zinc carbonate, basic zinc carbonate (also known as "hydroxy-containing zinc carbonate", also know as "zinc hydroxy carbonate" which is further identified by the empirical formula $Zn_5(OH)_6(CO_3)_2$), and combinations thereof.

The isothiazolinone useful in the present invention is preferably an isothiazolin-3-one that is selected from: 1,2-benzisothiazolin-3-one ("BIT"), N-(n-butyl)-1,2-benzisothiazolin-3-one ("BBIT"), 4,5-dichloro-2-n-octyl-4-isothiazolin-3-one ("DCOIT"), 2-methyl-4-isothiazolin-3-one ("MIT"), mixtures of 5-chloro-2-methyl-4-isothiazolin-3-one ("CIMIT") plus MIT (available from Rohm and Haas Company, Philadelphia, Pa. under the tradename Kathon®) dithio-2,2'-bis(benzmethylamide), and combinations thereof. Particularly preferred isothiazolins are BIT, MIT and BBIT, and combinations thereof.

In the composition, the isothiazolin-3-one is present in an amount of from 1 to 500 ppm (preferably from 5 to 500 ppm), the zinc compound is present in an amount of from 5 to 200,000 ppm (preferably from 5 to 500 ppm), and the weight ratio of the isothiazolin-3-one to the zinc compound is from 1:2000 to 100:1 (preferably from 100:1 to 1:100).

Optionally, the antimicrobial composition additionally comprises a pyrithione salt or pyrithione acid. Useful pyrithione salts include copper pyrithione, zinc pyrithione, sodium pyrithione. If used, the pyrithione salt or pyrithione acid is suitably present in the composition in an amount of from about 0.001% w/w to about 1.0% w/w.

In one embodiment, the combination of antimicrobial components for the antimicrobial composition can be provided in the form of an antimicrobial composition concentrate that, upon dilution with water, provides antimicrobial efficacy in a functional fluid. The concentrate comprises (a) at least one isothiazolin-3-one and (b) at least one zinc compound selected from the group consisting of zinc salts, zinc oxides, zinc hydroxides, and combinations thereof. In the concentrate, component (a) is present in an amount of from 1 to 95% w/w, and component (b) is present in an amount of from 1 to 50% w/w.

The antimicrobial compositions of the present invention are suitably used in functional fluids such as polymer emulsions, or other coating compositions, to impart both wet state and dry film preservation. The base medium can be, for example, a polymer useful in polymer emulsions wherein the polymer is selected from the group consisting of acrylic and substituted (meth)acrylates, styrene/butadiene, ethylene vinyl acetate, polyvinyl acetate, styrene/butadiene/N-methylol acrylamide, nitrile and copolymers of the aforementioned. Typical functional fluids include coating compositions, such as paints, adhesives, sealants, caulks, mineral and pigment slurries, printing inks, agricultural pesticide formulations, household products, personal care, metal working fluids and other aqueous based systems.

The invention is further described in the Examples given below. All percentages given herein are weight percents based on the total weight of the composition, unless otherwise stated. All patents referred to in this application are incorporated herein by reference in their entirety.

Example 1

In this example, samples of a commercial water based acrylic latex, trade name REVACRYL 1A, supplied by the Harlow Chemical Company, pH 8.1, containing antimicrobial additives in amounts as identified in Table I below, were challenged with a bacterial suspension consisting of Pseudomonas aeruginosa, NCIMB 8295
Providencia rettgeri, NCIMB 10842
Serratia marcescens, NCIMB 9523
Aeromonas hydrophila, NCIMB 9233
Alcaligenes spp. (Wet State Preservation isolate)
Burkholderia cepacia, ATCC 25416
Pseudomonas putida, NCIMB9494

All test species were cultured onto nutrient agar and incubated for 24 hours at 30° C. After this period individual suspensions of each test organism were prepared at a concentration of $10^6$ colony forming units per ml in saline solution by means of a Thoma counting chamber, achieved by mixing equal volumes of the individual suspensions. The concentration of bacteria in each aliquot after each challenge was $2\times10^6$ per ml.

The antimicrobial additive-containing paint samples were stored at 40° C. for 7 days prior to commencing the test. The paint samples were challenged with 1% v/v of bacterial suspension as described above. All test samples were incubated at 30° C. for the duration of the test and examined for viable bacteria after 1, 3 and 7 days after each challenge. Viable bacteria were detected by streaking aliquots onto nutrient agar followed by incubation at 30° C. for 2 days.

Table I presents the results obtained after the third inoculation days 1, 3 and 7.

TABLE I

| | | 3rd inoculation | | |
|---|---|---|---|---|
| Sample | BIT/ppm | Day 1 | Day 3 | Day 7 |
| BIT/ZnO | 50 | C | C | C |
| | 100 | 1+ (92) | 1+ (27) | – |
| | 150 | 1+ (95) | S (7) | – |
| | 200 | S (10) | T (4) | – |
| | 250 | 1+ (89) | 1+ (22) | – |
| | 300 | 1+ (77) | 1+ (12) | – |
| BIT/ZnCl2 | 50 | C | C | C |
| | 100 | ++ | 1+ (30) | – |
| | 150 | 1+ (34) | 1+ (21) | – |
| | 200 | 1+ (51) | 1+ (14) | – |
| | 250 | ++ (185) | 1+ (25) | – |
| | 300 | 1+ (58) | 1+ (17) | – |
| PROXEL BD20 | 50 | C | C | C |
| | 100 | C | C | C |
| | 150 | C | C | C |
| | 200 | C | C | C |
| | 250 | 1+ (75) | – | – |
| | 300 | 1+ (54) | – | – |
| | 400 | 1+ (47) | – | – |

Assessments are rated as:
– no growth detected
T 0-5 colonies present
S 5-10 colonies
1+ 20-100 colonies
+ light growth - no specified number of colonies
++ moderate growth - colonies visible, some coalescence
+++ heavy growth - coalescing colonies visible throughout
C confluent heavy growth Results demonstrate a potentiating effect of BIT in combination with a zinc containing salt when compared against a commercial product, namely PROXEL BD20 a product of Arch Chemicals, Inc. containing only BIT for the preservation of a commercial latex in that only 100 ppm of BIT is required in the presence of a zinc containing salt compared to 250 ppm of BIT for sample containing only BIT.

Example 2

Investigation of Potentiation Between 1,2-Benzisothiazolin-3-one (BIT) and Zinc Chloride ($ZnCl_2$) Against Pseudomonas aeruginosa Bacteria Pseudomonas aeruginosa (NCIB 10421) maintained on nutrient agar, were used to study the synergy between BIT and $ZnCl_2$.

Calculation of Minimum Inhibitory Concentrations Against Mono-Cultures

Bacteria were grown to stationary phase (approximately 24 hours) in nutrient broth (approximately $10^9$ organisms per ml). A 0.1% (v/v) inoculum was used to seed fresh medium and 100 µl of the inoculum was then added to each well of a microtitre plate, except for the first well which contained 200 µl.

Using doubling dilutions, the concentration of the compounds under investigation were varied in each well along the ordinate axis. The presence or absence of growth was recorded by visual inspection after 24 hours incubation at 37° C.

Calculation of Antimicrobial Activity Against Mono-Cultures

Microtitre plates were used for this assay. A simple matrix was constructed with varied concentrations of the two compounds from 2×MIC (minimum inhibitory concentration) down to zero concentration in a 10×10 array. As the microtitre plate has only 96 wells, the combinations of the two compounds that made up the extreme concentrations (highest and lowest) were omitted. Solutions were made up in broth at two times the final concentrations after pre-dissolving the compounds in distilled water.

The mixture (100 µl) was added to the plate so that the total volume in each well was 200 µl. Nutrient broth was used for Ps. aeruginosa. Plates were incubated for 16-24 hours at 37°. The presence or absence of growth was determined by visual inspection.

Results for Example 2

TABLE 2

Table 2: Antimicrobial Activity of Compounds Under Investigation

| | MIC (ppm) against Ps. aeruginosa | | | |
|---|---|---|---|---|
| COMPOUND | 1 | 2 | 3 | 4 |
| BIT | 30 | 42 | 42 | 30 |
| $ZnCl_2$ | 300 | 450 | 375 | 450 |

BIT is 1,2-benzisothiazolin-3-one available from Arch Limited PROXEL ® GXL.

Calculation of Activity Against Mono-Cultures

The Minimum Inhibitory Concentration (MIC) is the lowest concentration of biocide which showed growth inhibition when used alone. For the purpose of Fractional Inhibitory Concentration (FIC) calculations, if a single biocide did not control growth, the MIC was taken as the highest concentration used. A Fractional Inhibitory Concentration is the concentration of biocide which controlled growth in the mixture divided by the MIC of that biocide. FIC values for both compounds in the mixture were calculated and the results are shown in Table 3. The sum of these two figures gives an indication of the action of the two biocides. A value less than one indicates an enhanced effect, if the total is unity or greater the action is additive and if the value is greater than two the biocides are antagonistic.

TABLE 3

Fractional Inhibitory Concentrations for 1,2-Benzisothtazolin-3-one (BIT) and Zinc Chloride ($ZnCl_2$) against Ps. aeruginosa
Table 3

| | FIC VALUES | | | | | | | | | | | | |
|---|---|---|---|---|---|---|---|---|---|---|---|---|---|
| COMPOUND | 1 | | | 2 | | | | | 3 | | 4 | | |
| BIT | 1 | 0.20 | 0.20 | 0.40 | 0.14 | 0.14 | 0.29 | 0.29 | 0.43 | 0.14 | 0.20 | 0.40 | 0 |
| $ZnCl_2$ | 0 | 0.25 | 0.50 | 0.25 | 0.33 | 0.50 | 0.17 | 0.33 | 0.17 | 0.60 | 0.33 | 0.17 | 1 |
| Total | 1 | 0.45 | 0.70 | 0.65 | 0.47 | 0.64 | 0.46 | 0.62 | 0.60 | 0.74 | 0.53 | 0.57 | 1 |

Figure 1:
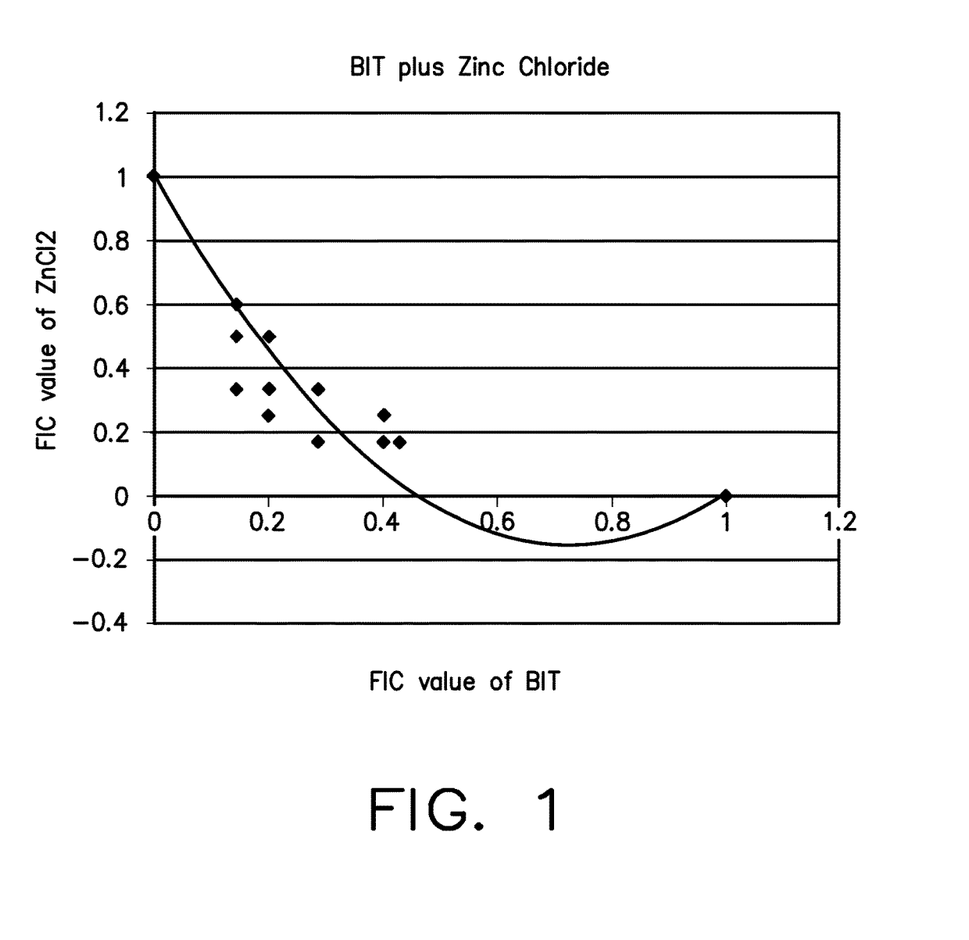
FIG. 1 provides a graphical depiction of an Isobologram showing Antimicrobial Activity of Mixtures of 1,2-Benzisothiazolin-3-one ("BIT") and Zinc Chloride against *Ps. aeruginosa* based on Fractional Inhibitory Concentration values.

If a graph with the axes representing the biocide Fractional Inhibitory Concentrations for the two biocides on linear scales is constructed, when the combination is additive the isobole (i.e. the line joining the points that represent all combinations with the same effect including the equally effective concentrations of the biocides used alone) is straight, enhanced combinations give concave isoboles and antagonistic combinations give convex isoboles. As shown in FIG. 1, the combination of BIT and $ZnCl_2$ has an enhanced effect against Ps. aeruginosa as confirmed by the concave isobole on the graph of FIG. 1.

Example 3

Investigation of Potentiation Between Kathon® (CIMIT/MIT) and Zinc Chloride ($ZnCl_2$) Against *Pseudomonas aeruginosa*

Bacteria

*Pseudomonas aeruginosa* (NCIB 10421) maintained on nutrient agar, were used to study the synergy of Kathon® and $ZnCl_2$.

Calculation of Minimum Inhibitory Concentrations Against Mono-Cultures

Bacteria were grown to stationary phase (approximately 24 hours) in nutrient broth (approximately $10^9$ organisms per ml). A 0.1% (v/v) inoculum was used to seed fresh medium and 100 μl of the inoculum was then added to each well of a microtitre plate, except for the first well which contained 200 μl.

Using doubling dilutions, the concentration of the compounds under investigation were varied in each well along the ordinate axis. The presence or absence of growth was recorded by visual inspection after 24 hours incubation at 37° C.

The mixture of CIMIT and MIT is available from Rohm and Haas Company, Philadelphia, Pa. under the tradename Kathon®.

Calculation of Synergy Against Mono-Cultures

The Minimum Inhibitory Concentration (MIC) is the lowest concentration of biocide which showed growth inhibition when used alone. For the purpose of Fractional Inhibitory Concentration (FIC) calculations, if a single biocide did not control growth, the MIC was taken as the highest concentration used. A Fractional Inhibitory Concentration is the concentration of biocide which controlled growth in the mixture divided by the MIC of that biocide. FIC values for both compounds in the mixture were calculated and the results are shown in Table 5. The sum of these two figures gives an indication of the action of the two biocides. A value less than one indicates an enhanced effect, if the total is unity or greater the action is additive and if the value is greater than two the biocides are antagonistic.

TABLE 5

Fractional Inhibitory Concentrations for Kathon (CIMIT/MIT) and Zinc Chloride ($ZnCl_2$) against *Ps. aeruginosa*
Table 5

| COMPOUND | FIC VALUES | | | | | | | | | | | |
|---|---|---|---|---|---|---|---|---|---|---|---|---|
| | 1 | | 2 | | 3 | | | 4 | | | | |
| Kathon | 1 | 0.17 | 0.17 | 0.33 | 0.33 | 0.17 | 0.33 | 0.33 | 0.14 | 0.28 | 0.28 | 0 |
| $ZnCl_2$ | 0 | 0.14 | 0.29 | 0.14 | 0.29 | 0.29 | 0.14 | 0.29 | 0.50 | 0.38 | 0.50 | 1 |
| Total | 1 | 0.31 | 0.46 | 0.47 | 0.62 | 0.46 | 0.47 | 0.62 | 0.64 | 0.66 | 0.78 | 1 |

Calculation of Antimicrobial Activity Against Mono-Cultures

Microtitre plates were used for this assay. A simple matrix was constructed with varied concentrations of the two compounds from 2×MIC (minimum inhibitory concentration) down to zero concentration in a 10×10 array. As the microtitre plate has only 96 wells, the combinations of the two compounds that made up the extreme concentrations (highest and lowest) were omitted. Solutions were made up in broth at two times the final concentrations after pre-dissolving the compounds in distilled water.

The mixture (100 μl) was added to the plate so that the total volume in each well was 200 μl Nutrient broth was used for *Ps. aeruginosa*. Plates were incubated for 16-24 hours at 37°. The presence or absence of growth was determined by visual inspection.

Results of Example 3

TABLE 4

Table 4: Antimicrobial Activity of Compounds Under Investigation

| | MIC (ppm) against *Ps. aeruginosa* | | | |
|---|---|---|---|---|
| COMPOUND | 1 | 2 | 3 | 4 |
| Kathon | 0.9 | 0.9 | 0.9 | 0.53 |
| $ZnCl_2$ | 294 | 294 | 210 | 600 |

Figure 2:
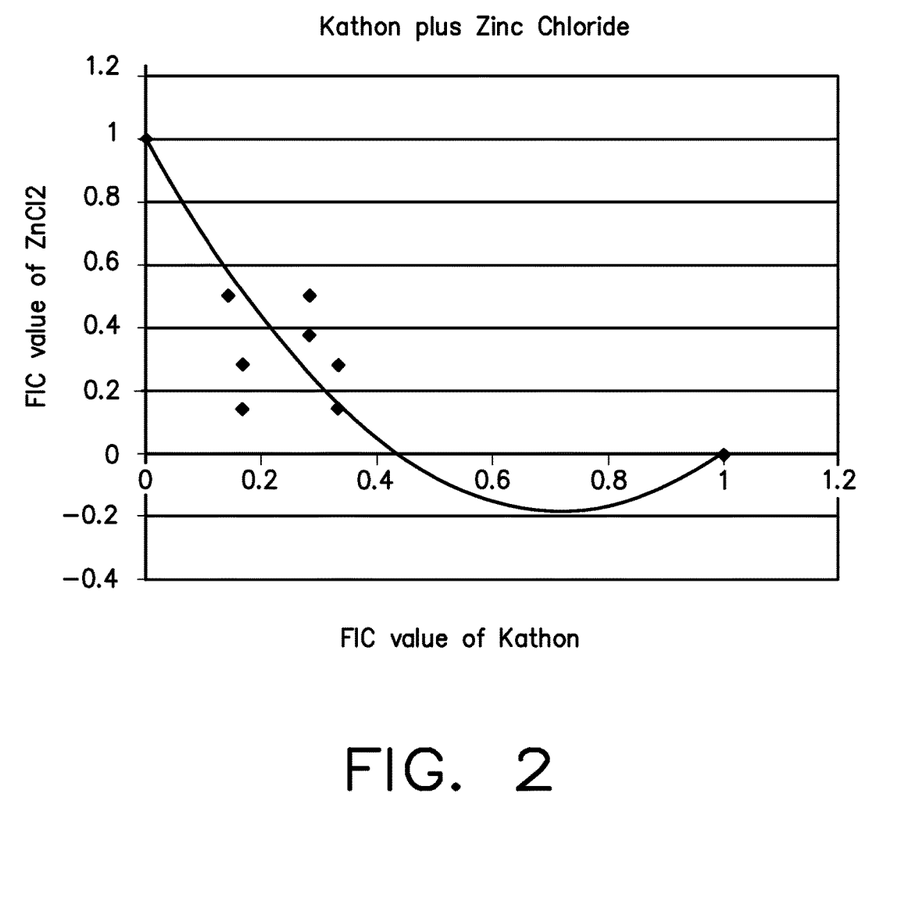
FIG. 2 provides a graphical depiction of an Isobologram showing Antimicrobial Activity of Mixtures of Kathon® (a mixture of 5-chloro-2-methyl-4-isothiazolin-3-one ("CIMIT") and 2-methyl-4-isothiazolin-3-one ("MIT")) and Zinc Chloride against *Ps. aeruginosa* based on Fractional Inhibitory Concentration values.

If a graph with the axes representing the biocide Fractional Inhibitory Concentrations for the two biocides on linear scales is constructed, when the combination is additive the isobole (i.e. the line joining the points that represent all combinations with the same effect including the equally effective concentrations of the biocides used alone) is straight, enhanced combinations give concave isoboles and antagonistic combinations give convex isoboles. As shown in FIG. 2, the combination of Kathon® and $ZnCl_2$ has an enhanced effect against *Ps. aeruginosa* as confirmed by the concave isobole in FIG. 2.

Example 4

Investigation of Potentiation Between MIT and Zinc Chloride ($ZnCl_2$) Against *Pseudomonas aeruginosa*

Bacteria

*Pseudomonas aeruginosa* (NCIB 10421) maintained on nutrient agar, were used to study the synergy between MIT and $ZnCl_2$.

Calculation of Minimum Inhibitory Concentrations Against Mono-Cultures

Bacteria were grown to stationary phase (approximately 24 hours) in nutrient broth (approximately $10^9$ organisms per ml). A 0.1% (v/v) inoculum was used to seed fresh medium and 100 μl of the inoculum was then added to each well of a microtitre plate, except for the first well which contained 200 μl.

Using doubling dilutions, the concentration of the compounds under investigation were varied in each well along the ordinate axis. The presence or absence of growth was recorded by visual inspection after 24 hours incubation at 37° C.

Calculation of Antimicrobial Activity Against Mono-Cultures

Microtitre plates were used for this assay. A simple matrix was constructed with varied concentrations of the two compounds from 2×MIC (minimum inhibitory concentration) down to zero concentration in a 10×10 array. As the microtitre plate has only 96 wells, the combinations of the two compounds that made up the extreme concentrations (highest and lowest) were omitted. Solutions were made up in broth at two times the final concentrations after pre-dissolving the compounds in distilled water.

The mixture (100 μl) was added to the plate so that the total volume in each well was 200 μl. Nutrient broth was used for Ps. aeruginosa. Plates were incubated for 16-24 hours at 37°. The presence or absence of growth was determined by visual inspection.

Results of Example 4

TABLE 6

Table 6: Antimicrobial Activity of Compounds Under investigation

| COMPOUND | MIC (ppm) against Ps. aeruginosa | | | |
|---|---|---|---|---|
| | 1 | 2 | 3 | 4 |
| MIT | 9 | 6 | 10.5 | 8 |
| $ZnCl_2$ | 210 | 210 | 450 | 450 |

Calculation of Synergy Against Mono-Cultures

The Minimum Inhibitory Concentration (MIC) is the lowest concentration of biocide which showed growth inhibition when used alone. For the purpose of Fractional Inhibitory Concentration (FIC) calculations, if a single biocide did not control growth, the MIC was taken as the highest concentration used. A Fractional Inhibitory Concentration is the concentration of biocide which controlled growth in the mixture divided by the MIC of that biocide. FIC values for both compounds in the mixture were calculated and the results are shown in Table 7. The sum of these two figures gives an indication of the action of the two biocides. A value less than one indicates an enhanced effect, if the total is unity or greater the action is additive and if the value is greater than two the biocides are antagonistic.

Figure 3:
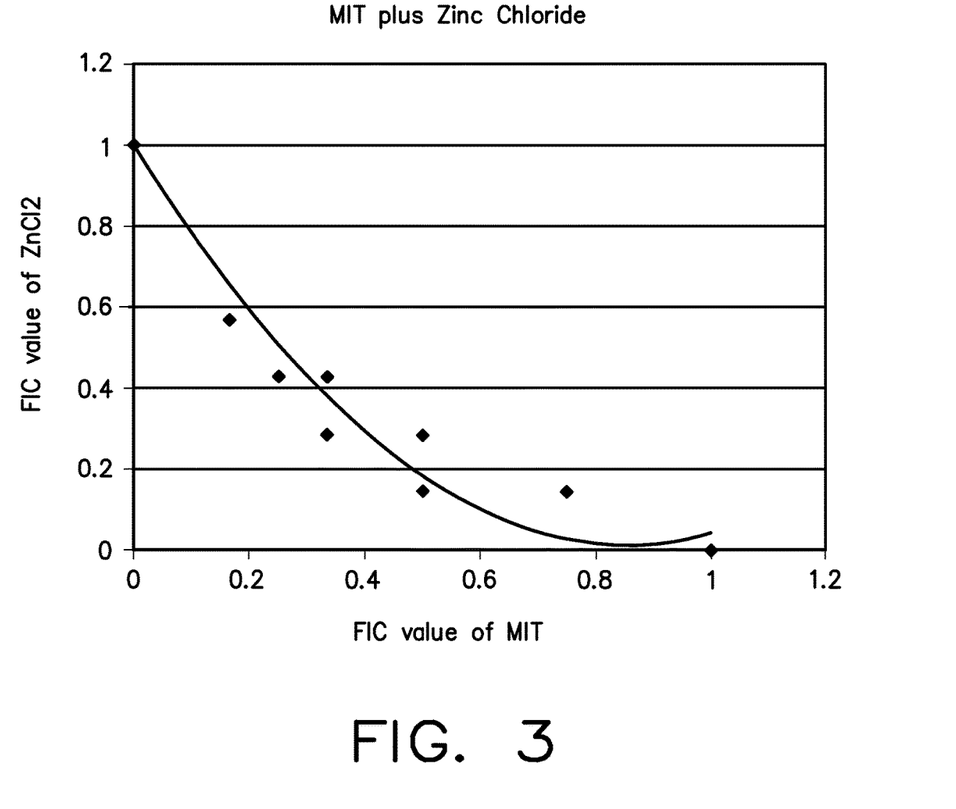
FIG. 3 provides a graphical depiction of an Isobologram showing Antimicrobial Activity of Mixtures of MIT and Zinc Chloride against *Ps. aeruginosa* based on Fractional Inhibitory Concentration values.

If a graph with the axes representing the biocide Fractional Inhibitory Concentrations for the two biocides on linear scales is constructed, when the combination is additive the isobole (i.e. the line joining the points that represent all combinations with the same effect including the equally effective concentrations of the biocides used alone) is straight, enhanced combinations give concave isoboles and antagonistic combinations give convex isoboles. As shown in FIG. 3, the combination of MIT and $ZnCl_2$ has an enhanced effect against Ps. aeruginosa as confirmed by the concave isobole in FIG. 3.

Example 5

Investigation of Potentiation Between BBIT and Zinc Chloride ($ZnCl_2$) Against Pseudomonas aeruginosa Bacteria Pseudomonas aeruginosa (NCIB 10421) maintained on nutrient agar, were used to study the synergy between BBIT and $ZnCl_2$.

Calculation of Minimum Inhibitory Concentrations Against Mono-Cultures

Bacteria were grown to stationary phase (approximately 24 hours) in nutrient broth (approximately $10^9$ organisms per ml). A 0.1% (v/v) inoculum was used to seed fresh medium and 100 μl of the inoculum was then added to each well of a microtitre plate, except for the first well which contained 200 μl.

Using doubling dilutions, the concentration of the compounds under investigation were varied in each well along the ordinate axis. The presence or absence of growth was recorded by visual inspection after 24 hours incubation at 37° C.

Calculation of Antimicrobial Activity Against Mono-Cultures

Microtitre plates were used for this assay. A simple matrix was constructed with varied concentrations of the two compounds from 2×MIC (minimum inhibitory concentration) down to zero concentration in a 10×10 array. As the microtitre plate has only 96 wells, the combinations of the two compounds that made up the extreme concentrations (highest and lowest) were omitted. Solutions were made up in broth at two times the final concentrations after pre-dissolving the compounds in distilled water.

The mixture (100 μl) was added to the plate so that the total volume in each well was 200 μl. Nutrient broth was used for Ps. aeruginosa. Plates were incubated for 16-24

TABLE 7

Fractional Inhibitory Concentrations for (MIT) and Zinc Chloride ($ZnCl_2$) against Ps. aeruginosa
Table 7

| COMPOUND | FIC Values | | | | | | | | | | | |
|---|---|---|---|---|---|---|---|---|---|---|---|---|
| | 1 | | | | 2 | | | | 3 | | 4 | |
| MIT | 1 | 0.17 | 0.33 | 0.33 | 0.50 | 0.25 | 0.50 | 0.75 | 0.14 | 0.29 | 0.17 | 0 |
| $ZnCl_2$ | 0 | 0.57 | 0.29 | 0.43 | 0.14 | 0.43 | 0.29 | 0.14 | 0.33 | 0.17 | 0.50 | 1 |
| Total | 1 | 0.74 | 0.62 | 0.76 | 0.64 | 0.68 | 0.79 | 0.89 | 0.48 | 0.46 | 0.67 | 1 | hours at 37°. The presence or absence of growth was determined by visual inspection.

Results of Example 5

TABLE 8

Table 8: Antimicrobial Activity of Compounds Under Investigation

| | MIC (ppm) against Ps. aeruginosa | | | |
|---|---|---|---|---|
| COMPOUND | 1 | 2 | 3 | 4 |
| BBIT | 315 | 360 | 42 | 180 |
| $ZnCl_2$ | 525 | 525 | 600 | 600 |

BBIT is N-(n-butyl)-1,2-benzisothiazolin-3-one.

Calculation of Synergy Against Mono-Cultures

The Minimum Inhibitory Concentration (MIC) is the lowest concentration of biocide which showed growth inhibition when used alone. For the purpose of Fractional Inhibitory Concentration (FIC) calculations, if a single biocide did not control growth, the MIC was taken as the highest concentration used. A Fractional Inhibitory Concentration is the concentration of biocide which controlled growth in the mixture divided by the MIC of that biocide. FIC values for both compounds in the mixture were calculated and the results are shown in Table 9. The sum of these two figures gives an indication of the action of the two biocides. A value less than one indicates an enhanced effect, if the total is unity or greater the action is additive and if the value is greater than two the biocides are antagonistic.

TABLE 9

Fractional Inhibitory Concentrations for BBIT
and Zinc Chloride ($ZnCl_2$) against Ps. aeruginosa
Table 9

| | FIC values | | | | | | |
|---|---|---|---|---|---|---|---|
| COMPOUND | 1 | 2 | | 3 | | 4 | |
| BBIT | 1 | 0.29 | 0.25 | 0.14 | 0.71 | 0.25 | 0 |
| $ZnCl_2$ | 0 | 0.43 | 0.43 | 0.50 | 0.38 | 0.38 | 1 |
| Total | 1 | 0.71 | 0.68 | 0.64 | 1.09 | 0.63 | 1 |

Figure 4:
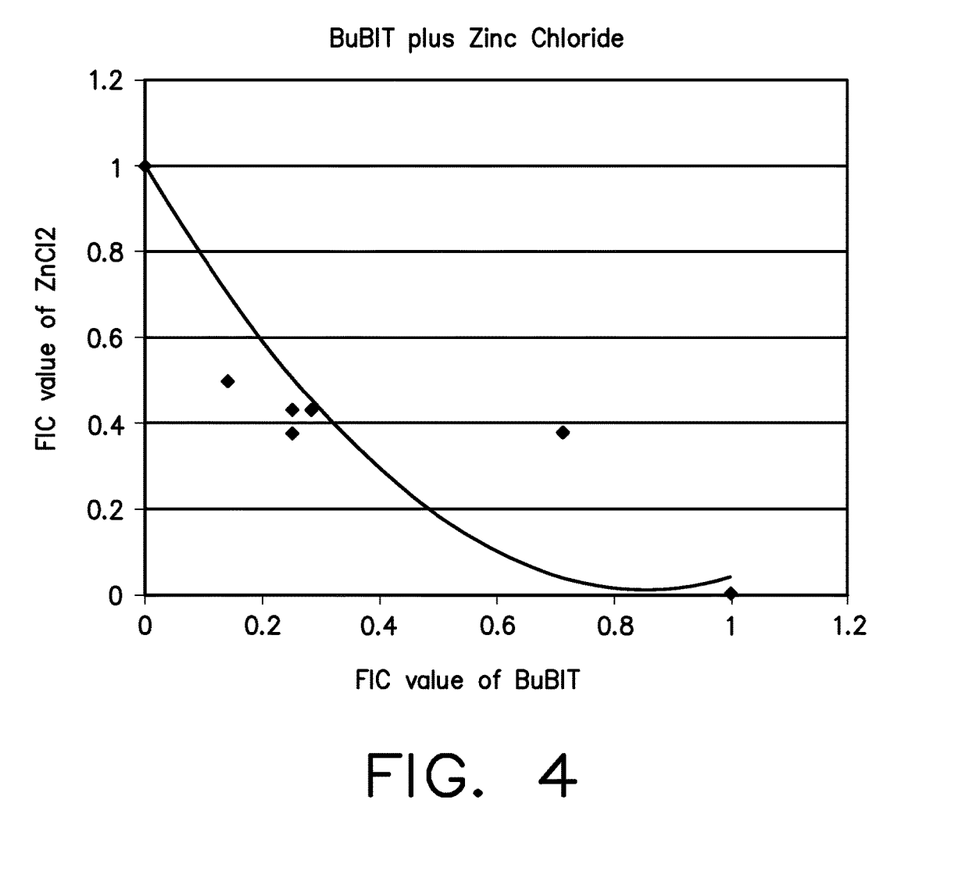
FIG. 4 provides a graphical depiction of an Isobologram showing Antimicrobial Activity of Mixtures of N-(n-butyl)-1,2-benzisothiazolin-3-one ("BBIT") and Zinc Chloride against *Ps. aeruginosa* based on Fractional Inhibitory Concentration values.

If a graph with the axes representing the biocide Fractional Inhibitory Concentrations for the two biocides on linear scales is constructed, when the combination is additive the isobole (i.e. the line joining the points that represent all combinations with the same effect including the equally effective concentrations of the biocides used alone) is straight, enhanced combinations give concave isoboles and antagonistic combinations give convex isoboles. As shown in FIG. 4, the combination of BBIT and $ZnCl_2$ has an enhanced effect against Ps. aeruginosa as confirmed by the concave isobole shown in FIG. 4.

Comparative Example A

Investigation of Potentiation Between 1,2-Benzisothiazolin-3-one (BIT) and Sodium Chloride ($NaCl_2$) Against Pseudomonas aeruginosa as Compared to the Synergy Between 1,2-Benzisothiazolin-3-one (BIT) and Zinc Chloride ($ZnCl_2$) Against Pseudomonas aeruginosa (Example 2)

Bacteria

Pseudomonas aeruginosa (NCIB 10421) maintained on nutrient agar, were used to study the efficacy of the combination of BIT with sodium chloride.

Calculation of Minimum Inhibitory Concentrations Against Mono-Cultures

Bacteria were grown to stationary phase (approximately 24 hours) in nutrient broth (approximately $10^9$ organisms per ml). A 0.1% (v/v) inoculum was used to seed fresh medium and 100 µl of the inoculum was then added to each well of a microtitre plate, except for the first well which contained 200 µl.

Using doubling dilutions, the concentration of the compounds under investigation were varied in each well along the ordinate axis. The presence or absence of growth was recorded by visual inspection after 24 hours incubation at 37° C.

Calculation of Antimicrobial Activity Against Mono-Cultures

Microtitre plates were used for this assay. A simple matrix was constructed with varied concentrations of the two compounds from 2×MIC (minimum inhibitory concentration) down to zero concentration in a 10×10 array. As the microtitre plate has only 96 wells, the combinations of the two compounds that made up the extreme concentrations (highest and lowest) were omitted. Solutions were made up in broth at two times the final concentrations after pre-dissolving the compounds in distilled water.

The mixture (100 µl) was added to the plate so that the total volume in each well was 200 µl. Nutrient broth was used for Ps. aeruginosa. Plates were incubated for 16-24 hours at 37°. The presence or absence of growth was determined by visual inspection.

Results of Comparative Example A

TABLE 10

Table 10: Antimicrobial Activity of Compounds Under Investigation

| COMPOUND | MIC (ppm) against Ps. aeruginosa |
|---|---|
| BIT | 30 |
| $NaCl_2$ | None detected (greater than 675) |

BIT is 1,2-benzisothiazolin-3-one available from Arch Limited as PROXEL$^{RTM}$ GXL.

Calculation of Potentiation Against Mono-Cultures

The Minimum Inhibitory Concentration (MIC) is the lowest concentration of biocide which showed growth inhibition when used alone. For the purpose of Fractional Inhibitory Concentration (FIC) calculations, if a single biocide did not control growth, the MIC was taken as the highest concentration used. A Fractional Inhibitory Concentration is the concentration of biocide which controlled growth in the mixture divided by the MIC of that biocide. FIC values for both compounds in the mixture were calculated and the results are shown in Table 11. The sum of these two figures gives an indication of the action of the two biocides. A value less than one indicates an enhanced effect, if the total is unity or greater the action is additive and if the value is greater than two the biocides are antagonistic.

TABLE 11

Table 11: Fractional Inhibitory Concentrations for 1,2-Benzisothiazolin-3-one (BIT) and Sodium Chloride ($NaCl_2$) against Ps. aeruginosa

| COMPOUND | | FIC VALUES | |
|---|---|---|---|
| BIT | 1 | 1.00 | 0 |
| $NaCl_2$ | 0 | 0.33 | 1 |
| Total | 1 | 1.33 | 1 |

Figure 5:
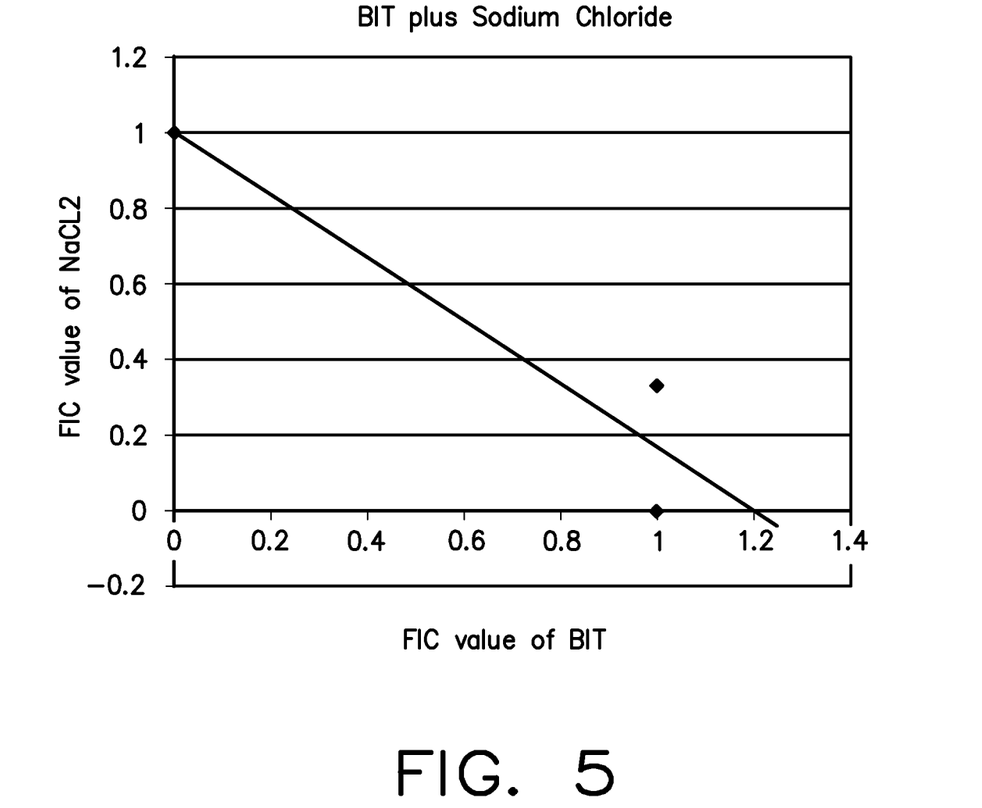
FIG. 5 provides a graphical depiction of an Isobologram showing Antimicrobial Activity of Mixtures of BIT and Sodium Chloride against *Ps. aeruginosa* based on Fractional Inhibitory Concentration values.

If a graph with the axes representing the biocide Fractional Inhibitory Concentrations for the two biocides on linear scales is constructed, when the combination is additive the isobole (i.e. the line joining the points that represent all combinations with the same effect including the equally effective concentrations of the biocides used alone) is straight, enhanced combinations give concave isoboles and antagonistic combinations give convex isoboles. As shown in FIG. 5, the combination of BIT and $NaCl_2$ is additive against *Ps. aeruginosa* as confirmed by the straight isobole in FIG. 5. Additionally, the results of this Example further illustrate that the combination of an isothiazolin-3-one such as BIT and a zinc compound such as $ZnCl_2$, as shown in Example 2, show unexpected potentiation results against *Ps. aeruginosa*.

What is claimed is:

1. An antimicrobial composition concentrate comprising:
   (a) at least one isothiazolin-3-one comprising 1,2-benzisothiazolin-3-one, N-(n-butyl)-1,2-benzisothiazolin-3-one, or a mixture thereof; and
   (b) at least one zinc compound comprising a zinc oxide,
   wherein the isothiazolin-3-one is present in an amount of from about 1% to about 95% w/w based on the total weight of the concentrate,
   wherein the zinc compound is present in an amount from about 1% to about 50% w/w based on the total weight of the concentrate, and
   wherein the weight ratio of the isothiazolin-3-one to the zinc compound is from 1:100 to 100:1.

2. The antimicrobial composition concentrate of claim 1, wherein the isothiazolin-3-one comprises 1,2-benzisothiazolin-3-one.

3. The antimicrobial composition concentrate of claim 1, wherein the isothiazolin-3-one comprises N-(n-butyl)-1,2-benzisothiazolin-3-one.

4. The antimicrobial composition concentrate of claim 1, further comprising a co-biocide comprising a pyrithione compound comprising a pyrithione salt, a pyrithione acid, or a combination thereof, wherein the co-biocide is present in the composition concentrate in an amount of from about 1% to about 50% w/w based on the total weight of the composition concentrate.

5. The antimicrobial composition concentrate of claim 4, wherein the pyrithione compound comprises zinc pyrithione.

6. The antimicrobial composition concentrate of claim 4, wherein the isothiazolin-3-one comprises 1,2-benzisothiazolin-3-one.

7. The antimicrobial composition concentrate of claim 4, wherein the pyrithione compound comprises copper pyrithione, sodium pyrithione, or a mixture thereof.

8. The antimicrobial composition concentrate of claim 4, wherein the isothiazolin-3-one comprises N-(n-butyl)-1,2-benzisothiazolin-3-one.

9. The antimicrobial composition concentrate of claim 1, wherein the zinc compound is present in an amount greater than the isothiazolin-3-one.

10. An antimicrobial composition concentrate comprising:
    (a) 1,2-benzisothiazolin-3-one,
    (b) zinc oxide, and
    (c) zinc pyrithione,
    wherein the 1,2-benzisothiazolin-3-one is present in an amount of from about 1% to about 95% w/w based on the total weight of the concentrate,
    wherein the zinc oxide is present in an amount from about 1% to about 50% w/w based on the total weight of the concentrate, and
    wherein the zinc pyrithione is present in an amount from about 1% to about 50% w/w based on the total weight of the concentrate,
    wherein the weight ratio of the isothiazolin-3-one to the zinc compound is from 1:100 to 100:1.

* * * * *

UNITED STATES PATENT AND TRADEMARK OFFICE
CERTIFICATE OF CORRECTION

PATENT NO. : 9,717,250 B2  
APPLICATION NO. : 13/850672  
DATED : August 1, 2017  
INVENTOR(S) : Thompson et al.

Page 1 of 1

It is certified that error appears in the above-identified patent and that said Letters Patent is hereby corrected as shown below:

In the Claims

At Claim 10, Column 14, Lines 35 to 36, delete "isothiazolin-3-one to the zinc compound" and insert --1,2-benzisothiazolin-3-one to the zinc oxide--

Signed and Sealed this  
Eighth Day of December, 2020

Andrei Iancu  
*Director of the United States Patent and Trademark Office*